United States Patent [19]

Cote et al.

[11] Patent Number: 4,695,538
[45] Date of Patent: Sep. 22, 1987

[54] HUMAN MONOCLONAL ANTIBODIES TO CELL SURFACE ANTIGENS

[75] Inventors: Richard J. Cote; Timothy M. Thomson; Alan N. Houghton, all of New York, N.Y.; Herbert F. Oettgen, New Canaan, Conn.; Lloyd J. Old; Carlos C. Cardo, both of New York, N.Y.

[73] Assignee: Sloan-Kettering Institute for Cancer Research, New York, N.Y.

[21] Appl. No.: 616,397

[22] Filed: Jun. 1, 1984

[51] Int. Cl.$^4$ ............... G01N 33/53; G01N 33/577
[52] U.S. Cl. ............................. 435/7; 424/1.1; 424/3; 424/7; 435/68; 435/172.2; 435/240.27; 935/89; 935/93; 935/95; 935/96; 935/99; 935/100; 935/101; 935/106; 935/107; 935/108; 935/110; 436/501; 436/504; 436/536; 436/537; 436/518; 436/548; 436/813; 436/828
[58] Field of Search ............... 436/548, 504, 501, 536, 436/537, 518, 813, 828; 424/1.1, 9, 3, 7; 435/6, 7, 68, 240, 172.2; 935/89, 93, 95, 96, 99–101, 106–108, 100

[56] References Cited

U.S. PATENT DOCUMENTS 4,443,427 4/1984 Reinherz et al. ............... 424/1.1
4,513,088 4/1985 Levy et al. ............... 436/518
4,529,694 7/1985 Lazarus et al. ............... 935/100

FOREIGN PATENT DOCUMENTS 28902 5/1981 European Pat. Off. ............... 435/68

OTHER PUBLICATIONS

Houghton et al., J. Exp. Med., 158 (Jul. 1983) 53–65.
Cote et al., Proc. Natl. Acad. Sciences U.S.A., 80 (Apr. 1983), 2026–30.
Dippold et al., Proc. Natl. Acad. Sci. U.S.A., 77 (Oct. 1980), 6114–8.
Daar et al., The Lancet, Aug. 29, 1981, 434–8.
Croce et al., Proc. Natl. Acad. Sci. U.S.A., 76 (Jul. 1979), 3416–9.

*Primary Examiner*—Christine M. Nucker
*Attorney, Agent, or Firm*—John P. White

[57] ABSTRACT

Human monoclonal antibodies (HmAbs) capable of reacting with cell surface antigens and intracellular components are disclosed. It has been found that HmAbs Ev248, Ch-5, Ch-13, Te-39, Hu44, Ge-1, Gr-431, Gr169 and Sp909 may be used to detect these antigens in various cells. By means of these HmAbs malignant cells may be determined. This information may be used to screen metastasized tumors and primary tumors for tissue source and greatly affects the management of these cancers.

12 Claims, No Drawings

HUMAN MONOCLONAL ANTIBODIES TO CELL SURFACE ANTIGENS

The present invention was wholly or partially made with funds provided by the National Cancer Institute, Department of Human Health and Services. Accordingly, the United States Government has certain rights in this invention.

This invention concerns hybridomas which produce human monoclonal antibodies recognizing surface antigens and intracellular components of human cells. These human monoclonal antibodies are useful in diagnosis of cancer.

BACKGROUND

Monoclonal antibodies are highly specific, sensitive reagents for identifying proteins. Knowledge about the surface antigenic structure of several types of human cancers has advanced rapidly with mouse monoclonal antibodies as serological probes, and application of these reagents to cancer diagnosis and therapy is underway. Production of human monoclonal antibodies, however, has proved more difficult to achieve. Despite much effort by many laboratories around the world, there are relatively few reports of success in the literature.

Human monoclonal antibodies which recognize cell surface and intracellular antigens derived from lymphocytes of patients with malignant melanoma have been reported (Houghton, et al, J. Exp. Med. July, 1983). Human monoclonal antibodies recognizing other cellular antigens have been made from lymphocytes of normal individuals or individuals having renal cancer, lung cancer, breast cancer or lymphoproliferative disease, (Cote, et al. Pro Nat'l. Acad. Sci. April, 1983). Other human monoclonal antibodies capable of detecting hitherto unknown cell surface and intracellular antigens have been sought.

The human monoclonal antibody producing hybridoma cell lines of the present invention were formed by fusing a mouse myeloma cell line or human lymphoblastoid cell line with human lymphocytes from normal individuals and from individuals having breast cancer, colon cancer, lung cancer, melanoma or renal cancer. The lymphocytes were obtained from peripheral blood lymphocytes from normal individuals or individuals having renal cancer, spleen cells from individuals with lymphoproliferative disease or renal cancer and tumor specimen and or lymph node specimen from lung breast, renal cancer and melanoma were also used in the fusions.

These HmAbs recognize cell surface antigens or cytoplasmic components of human cells and are useful for detecting malignant cells as well as differentiating between tissue source of malignant cells.

HmAbs recognizing cell surface antigens and cytoplasmic components are antibodies Ev248, Ch5, Ch13, Te39, Hu44, Ge1, Gr169, Sp909 and Gr431. A panel comprised of these HmAbs has been formed.

A preferred embodiment of the present invention comprises a method for distinguishing between normal and malignant human cells comprising immunoassay of the Ev248 antigenic system with the HmAb Ev248. The Ev248 antigen is found on solid tumor cell lines and is restricted to epithelial cells but is not present on solid tumors of mesenchymal or neuroectodermal origin. It is thus useful in distinguishing solid tumors of epithelial origin such as breast cancers from melanoma which is of neuroectodermal origin.

HmAb Gr169 and reacts with a cell surface antigen of various cancers; Sp909 reacts a wide cell surface antigen on a wide variety of cells; Te39, Hu44, Gr431, Ch13, Ge1 and Ch5 react with intracellular components of various cancer cells; Sp909 Ch5, Ge1 and Ch13 also react with components of normal cells. These HmAbs are useful screening agents for cancer cells. Panels have been formed for this purpose.

The assay of the present invention comprises contacting cells with the antibody recognizing cell surface antigens, or cytoplasmic components and observing the reaction between said monoclonal antibody and said antigen. In a preferred embodiment of the present invention the tissue to be assayed is first excised and is then either freshly or after being frozen or embedded in paraffin by methods well-known in the art contacted with said monoclonal antibodies. In this embodiment said antibodies may be tagged with colored groups or color forming substances such as enzymes, preferably peroxidase and its substractes, with fluorescent substances or with radioactive elements by which the location of the antibodies may be traced. Serological assay of excised tissue is also an embodiment of the present invention. Thus passive hemmaglutination, antibody inhibition assay, or glycolipid-mediated immune adherence assay may be used. Likewise and anti-humas immunoglobulin assays and Protein A assays may be employed.

DESCRIPTION

The preparation of HmAbs used in the method of the present invention has been reported by the inventors and others (Houghton, et al. J. Exp. Med. (1983)). This publication is hereby incorporated by reference.

Abbreviations:

LICR-2, LICR-LON-HMy2; Ig, immunoglobulin; PHA, phytohemagglutinin; FCS, fetal calf serum; PA, protein A; IA, immune adherence; anti-Ig, rabbit anti-human Ig; EBV, Epstein-Barr virus; PBS, phosphate buffered saline; HmAb(s), human monoclonal antibody(ies); IF, intermediate filament; GFAP, glial fibrillary acidic protein.

The following description is intended to illustrate this invention without limiting same in any manner especially with respect to substantially functional equivalents of cell lines described and claimed herein.

Availability of Hybridoma Cell Lines

The cell lines disclosed in the present invention are deposited at the American Type Culture Collection, Bethesda, Md. and will be maintained in accordance with the Budapest Convention. They bear the following deposit numbers:

| Sloan-Kettering # | ATCC # |
| --- | --- |
| EV248 | HB 8565 |
| Ge1 | HB 8574 |
| Ch5 | HB 8572 |
| Ch13 | HB 8573 |
| Te39 | HB 8577 |
| Hu44 | HB 8576 |
| Gr431 | HB 8575 |

Deposit is for the purpose of enabling disclosure only and is not intended to limit the concept of the present invention to the particular materials deposited.

Preparation of Hybridomas

Cell Lines.

The ARH-77 derived LICR-2 human lymphoblastoid line was kindly provided by Drs. M. O'Hare, P. Edwards and A. M. Neville, the London Branch of the Ludwig Institute for Cancer Research. The mouse myeloma line, NS-1, was obtained in 1979 from Dr. U. Hammerling, Sloan-Kettering Institute for Cancer Research. This cell line is also on deposit at the ATCC. Characteristics of these cell lines are:

| CELL LINE | HEAVY CHAIN | LIGHT CHAIN | DOUBLING TIME | KARYOTYPE |
|---|---|---|---|---|
| LICR-2 | α | K | 24 hr | human |
| NS-1 | — | K | 24 hr | mouse |

The cells were cultured in RPMI 1640 supplemented with 7.5% fetal calf serum, 1% nonessential amino acids (GIBCO, Grand Island, NY), 100 U/ml penicillin, 100 g/ml streptomycin and 20 g/ml 8-azaguanine. No growth occurred in medium containing $4 \times 10^{-7}$M aminopterin.

Source of Lymphocytes.

Sterile specimens were obtained from the Pathology Department of Memorial Hospital through the Tumor Procurement Service. Lymphocytes were derived from (a) regional lymph nodes (patients with breast cancer, colon cancer, lung cancer, melanoma, and renal cancer); (b) peripheral blood (six patients with renal cancer and three normal individuals); (c) spleen (four patients with lymphoproliferative disease and one patient with renal cancer); and (d) tumor specimens (four lung cancers, four breast cancers and one malignant plural effusion from breast cancer).

Preparation of Lymphocytes.

Tumor, lymph nodes and spleen were freed of surrounding normal tissue under sterile conditions, and the specimens were minced and passed through 500 Mm cell sieves. The resultant suspension was pelleted, resuspended in RPMI 1640, layered on Ficoll-Hypaque (Pharmacia, Piscataway, NJ), and centrifuged at 400X g for 20 min. The interface cell population was washed and used as source of lymphocytes for fusion. Peripheral blood lymphocytes were similarly separated on Ficoll-Hypaque gradients. Lymphocytes ($1-2 \times 10^6$ cells/ml) were incubated in RPMI 1640 medium with 7.5% FCS at 37° C. for 24-48 hrs prior to fusion.

Cell Fusion.

Lymphocytes and the myeloma/lymphoblastoid cells were combined at a 1:1 or 2:1 ratio and washed three times in RPMI 1640. After the final wash, the supernatant was decanted and 0.2 ml 42% (w/v) polyethylene glycol (m.w. 4000) [in phosphate-buffered saline (PBS) containing 15% (v/v) DMSO] was added slowly to the cell pellet with gentle mixing for 3 min at 37° C. Ten ml RPMI 1640, 15% FCS, penicillin/streptomycin, nonessential amino acids, $2 \times 10^{-5}$M 2-mercaptoethanol, $1 \times 10^{-4}$ hypoxanthine and $1.6 \times 10^{-5}$M thymidine). The cells were incubated overnight at 37° C., pelleted, resuspended in post-fusion medium containing $4 \times 10^{-7}$M aminopterin and plated in 96 well tissue culture plates (Costar 3596) at a density of $1-2 \times 10^5$ lymphocytes/well on feeder layers of BALB/c or C57BL/6 peritoneal cells ($1 \times 10^5$ cells/well, plated 24-48 hrs previously). The medium was changed once a week, and the cells maintained in the presence of $4 \times 10^{-7}$M aminopterin for 4-6 weeks.

Fusion Conditions:

General Comments. A number of factors in the fusion procedure were analyzed. Because of variability from fusion to fusion, firm conclusions regarding optimal conditions are difficult to reach. However, several factors were found to influence results in a generally consistent fashion. These included: (1) Condition of myeloma/lymphoblastoid lines. The lines were maintained in log phase growth at 85% cell viability; fusions with overgrown cultures resulted in a low frequency of clonal outgrowth. (2) Fusion ratios. Lymphocyte: myeloma/lymphoblastoid cell ratios of 1:1 or 2:1 resulted in 2-8 times greater clonal outgrowth than fusions at 5:1 or 10:1. (3) Time of aminopterin addition. A delay in the addition of aminopterin to the fused cells for 24 hrs resulted in more vigorous growth of clones. (4) Fetal calf serum (FCS). Significant differences in the frequency of clonal outgrowth were found with different lots of FCS. As initially observed by Edwards et al. (Edwards, P. A. W., Smith, C. M., Neville, A. M. & O'Hare, M. J. (1982) Eur. J. Immunol. 12: 641–648), some lots of FCS inhibited the growth and clonability of the myeloma/lymphoblastoid cell lines and the growth of Ig-secreting clones derived from fusions. Lots of FCS were therefore prescreened for optimal growth-promoting properties using these cell types. Optimum fusion success rate was obtained with FCS concentrations of about 10% to 15%. (5) Other media supplements. Medium conditioned by several different cell types did not improve the frequency of clonal outgrowth. Supernatant from cultures of peripheral blood mononuclear cells stimulated 4-6 days with PHA and added to the post-fusion medium resulted in a marked reduction in resulting clones.

Results of Fusions with NS-1 and LICR-2

Clones derived from NS-1 generally appeared between 2-4 wks after fusion, while clones derived from LICR-2. All but one fusion between human lymphocytes and NS-1 resulted in growth (95%), while 79% of fusions with LICR-2 resulted in growth (Table I). Fusions of LICR-2 with peripheral blood lymphocytes gave the poorest results, with only 60% and 40% of fusions resulting in growth, respectively. For a given number of lymphocytes, fusions with NS-1 resulted in an average of eight times more clones than fusions with LICR-2.

Immunoglobulin Detection and Quantitation

Supernatants were screened for the production of human Ig by an enzyme-linked immunoassay. Falcon 3034 plates were precoated with 10 μl of supernatant from wells containing growing clones and incubated overnight at 4° C. The plates were washed with PBS and 10 μl of alkaline phosphatase conjugated goat anti-human α, μ or γ heavy chain-specific antibody (Sigma Chemical Co., St. Louis, MO) was added to each well (1/100 dilution). For determination of total Ig, the class-specific reagents were combined (final dilution of each reagent 1/100). After a 30 min. incubation at 37° C., the plates were washed, and 10 μl of p-nitrophenyl disodium phosphate (1 mg/ml) in 10% diethanolamine buffer (pH 9.6) was added to each well and incubated for 30 min. at 37° C. Color changes were measured by an Artek Model 210 Reader. The test was specific for each Ig class over a range of 500 ng/ml to 50 g/ml. For detection of intracellular κ- or λ light chains by indirect immunofluorescence (see below), goat antihuman κ or λ light chain antibodies conjugated to FITC (Cappel Laboratories, Cochranville, PA) was used (1/40 dilution).

Serological Assays for Cell Surface and Intracellular Antigens

The protein A (PA), immune adherence (IA) and rabbit antihuman Ig (anti-Ig) red cell rosetting assay and absorption tests for the detection of cell surface antigens have been described previously (Shiku, H., Takahashi, T., Oettgen, H. F. & Old, L. J. (1976) J. Exp. Med. 144: 873-881, Pfreundschuh, M. G., Ueda, R., Rauterberg, E. W., Dorken, B. H. & Shiku, H. (1980) J. Immunol. Metho. 37: 71-81., Albino, A. P., Lloyd, K. O., Houghton, A. N., Oettgen, H. F. & Old, L. J. (1981) J. Exp. Med. 154: 1764-1778. Intracellular antigens were detected by indirect immunofluorescene tests with target cells grown to confluency in Falcon 3034 plates. The plates were washed and the cells fixed with a 1:1 methanol:acetone (v/v) solution for 5 min. at room temperature. 10 $\mu$l of the supernatant to be tested was plated into each well and incubated for 1 hour at room temperature. The cells were washed and 10 $\mu$l of a goat antihuman Ig conjugated to FITC (DAKO, Copenhagen) was added to each well (1/40 dilution) and incubated for 1 hour at room temperature. After washing, fluorescence was evaluated with a Leitz Dialux 20 fluorescent microscope. The human cell lines used in the serological assays have been described previously (Shiku, H., Takahashi, T., Oettgen, H. F. & Old, L. J. (1976) J. Exp. Med. 144: 873-881, Albino, A. P., Lloyd, K. O., Houghton, A. N., Oettgen, H. F. & Old, L. J. (1981) J. Exp. Med. 154: 1764-1778, Ueda, R., Ogata, S. I., Morrissey, D. M., Finstead, C. L., Szkudlarek, J., Whitmore, W. F., Jr., Oettgen, H. F., Lloyd, K. O. & Old, L. J. (1981) Proc. Nat'l. Acad. Sci., U.S.A. 78: 5122-5126).

Immunoglobulin Secretion: Range and Stability

Wells with growing clones were screened for Ig secretion; 20–80% contained 500 ng Ig/ml supernatant. [The level of chain secreted by the LICR-2 line (100 ng/ml) was generally below the sensitivity of our Ig assay. However, the possibility that the production of LICR-2-derived chain may be increased following fusion cannot be excluded. Human and mouse light chains $\epsilon$ and heavy chains were not detected in these assays. The levels of Ig produced by the clones were similar regardless of the myeloma/lymphoblastoid cell line or the source of lymphocytes. Seventy to 75% of Ig-secreting clones produced between 1–10 g Ig/ml and 25–30% produced between 11–100 $\mu$g/ml. In 80–90% of wells, only one class of Ig could be detected. The relative proportion of clones secreting each of the major Ig classes (IgM, IgG, IgA) was independent of the myeloma/lymphoblastoid fusion partner, but appeared to be influenced by the source of lymphocytes. A difference was found between clones derived from peripheral blood lymphocytes and those derived from axillary lymph nodes of patients with breast cancer. A higher proportion of IgA-secreting clones resulted from fusions with axillary lymph nodes, while the proportion of IgM-secreting clones was generally higher in fusions with peripheral blood lymphocytes.

The stability of Ig secretion by cells derived from fusions with NS-1 and LICR-2 was compared over a 2-3 month period of subculturing, the percentage of cultures continuing to secrete Ig was comparable (62-70%) in the case of the two fusion partners. At four and seven months post-fusion, approximately 50% of cultures from NS-1 and LICR-2 fusions continued to produce Ig. Thirty-two NS-1 and 19 LICR-2-derived cultures secreting Ig at two months were cloned (one cell/well) once or twice and stable Ig-secreting clones could be selected in 70-80% of cases (observation period 5 months).

Human Monoclonal Antibodies Reactive With Cell Surface Antigens

Cultures from fusions of human lymphocytes with NS-1 and LICR-2 have been identified that secrete antibody reactive with cell surface antigens. Fusions of NS-1 with lymphocytes from the spleen of a patient with renal autoimmune disease resulted in HmAb Ev248. This HmAb detects a cell surface antigen on malignant cells that is not present on normal cells tested. On solid tumor cells the antigen is restricted to epithelial cells and is not found on solid tumors of mesenchymal or neuroectodermal origin (Table III). On cells of hematopoietic origin, the Ev248 HmAb detects antigen on all or most hematopoietic malignancies. It is also on all EBV transformed (Epstein-Barr Virus) B cells. However, the Ev248 antigen has not been detected on any non-malignant cells of hematopoietic origin (B cells, T cells, macrophages granulocytes, platelets, erythrocytes). (Table II) The Ev248 antigen is a lipid. Its distribution indicates that this is a Class II tumor antigen (Old, L., Cancer Research 41 (361-375) (1981).

HmAb Ev248 is useful in the diagnosis of cancer. Immunoassay of cells for the Ev248 antigen is a means for distinguishing between normal and malignant cells and also for distinguishing tumors of epithelial origin from tumors of mesenchymal or neuroectodermal origin. (Table III). This assay is especially important in the diagnosis of metastasized tumors where the source of primary cancer may determine management and treatment protocol of the tumor. Assay with HmAb Ev248 is also useful for distinguishing normal from malignant cells of hematopoietic origin.

HmAb Ge-1 is prepared by fusion of LICR-2 with lymphocytes from lymph nodes of an individual having lung cancer (Table III). This HmAb detects an intracellular antigen on lung cancer cells and mesenchymally or neuroectodermally derived tumors. It is therefore useful in diagnosis of these cancers.

TABLE I

|  | Ig Class | Fusion Partner | Lymphocyte Source |
| --- | --- | --- | --- |
| Ev248 | IgM | NS-1 | Spleen, Renal autoimmune disease |
| Ch5 | IgM | NS-1 | Lymph node, colon cancer |
| Te39 | IgM | NS-1 | Lymph node, colon cancer |
| Hu44 | IgA | LICR-2 | Lymph node, breast cancer |
| Gr431 | IgM | NS-1 | Lymph node, breast cancer |
| Ch13 | IgM | NS-1 | Lymph node, colon cancer |
| Ge1 | IgA | LICR-2 | Lymph node lung tumor, |

Human Monoclonal Antibodies Reactive With Intracellular Antigens

Fusion of NS-1 or LICR-2 with lymphocytes from lymph node of individuals with colon or breast cancer result in hybridomas which secrete HmAbs which react with intracellular antigens (Table I). The cell lines which contain antigenic systems CA5, Te39, Hu44, Gr431, and Ch13 and react with these antibodies respectively are give in Table V.

TABLE II
CELL SURFACE ANTIGENS RECOGNIZED BY HUMAN MONOCLONAL ANTIBODIES DISTRIBUTION ON CELLS OF HEMATOPOIETIC ORIGIN*

| | Ev248 |
|---|---|
| PERIPHERAL BLOOD | |
| B cells | o o o o o |
| T cells | o o o o o |
| macrophages | o o o |
| granulocytes | o o o o |
| erythrocytes | o o o o o |
| LYMPH NODE | |
| B cells | o o |
| T cells | o o |
| SPLENOCYTES | o |
| EBV-TRANSFORMED CELLS | ● ● ● ● |
| LYMPHOMAS AND LEUKEMIAS | |
| B cell | ● ● ● ● |
| T cell | ● ● ● ● |
| Null | ● ● |

*Each circle represents a different cell line.
Results:
  o Antigen recognized by this antibody is not present.
  ● Antigen recognized by this antibody is detectable
  ◐ Antigen recognized by this antibody is poorly expressed.

TABLE III
Ev248 CELL SURFACE ANTIGEN DEFINED BY HUMAN MONOCLONAL ANTIBODY

| BREAST CANCER | | CERVICAL CANCER | |
|---|---|---|---|
| MCF-7 | + | ME-180 | + |
| BT-20 | + | OVARIAN CANCER | |
| Cama | + | SK-OV-3 | + |
| MDA-MB-231 | + | OV-2774 | + |
| SK-Br-7 | + | MELANOMA | |
| COLON CANCER | | SK-MEL-19 | − |
| SW48 | + | SK-MEL-28 | − |
| SW1083 | − | SK-MEL-37 | − |
| SW1116 | + | SK-MEL-64II | − |
| SW1222 | + | ASTROCYTOMA | |
| LUNG CANCER | | SK-MG-1 | − |
| SK-LC-6 | − | SK-MG-4 | − |
| SK-LC-15 | + | U251-MG | − |
| SK-LC-17 | − | NEUROBLASTOMA | |
| SK-LC-21 | + | LAN-1S | − |
| RENAL CANCER | | SMS-KAN | − |
| SK-RC-6 | − | SMS-SAN | − |
| SK-RC-7 | − | FIBROBLASTS | |
| SK-RC-29 | + | AS | − |
| BLADDER CANCER | | AX | − |
| TCC-SUP | + | EN | − |
| T-24 | − | | |

+: Antigen recognized by this antibody is present.
−: Antigen recognized by this antibody is not detectable.

TABLE IV
HUMAN MONOCLONAL ANTIBODIES REACTIVE WITH CELL SURFACE ANTIGENS

| CELL LINES | Ev248 | Gr169 | Sp909 |
|---|---|---|---|
| BREAST CANCER | ●o●o● | ●●●● | ●●o● | ●●●● |
| COLON CANCER | o●oo● | o●● | oo● | ●●● |
| LUNG CANCER | ●●oo● | o●●● | ●●o● | ●●●● |
| RENAL CANCER | o●●● | oo● | ●●● | ●●● |
| BLADDER CANCER | oooo | ●o●o | o●●● | ●●●● |
| OVARIAN CANCER | ●●●● | o●● | ●●● | ●●● |
| UTERINE/CERVICAL CANCER | ●o● | ●● | o | ● |
| MELANOMA | | | | |
| ASTROCYTOMA | ● | oooo | oooo | ●●●● |
| HEMATOPOIETIC TUMORS | ●● | ooo | ●●● | ●●● |
| EBV-TRANSFORMED CELLS | ●● | ●●● | | |
| FIBROBLASTS | | ●●● | ooo | ●●● |
| NORMAL KIDNEY | | oooo | oooo | ●●●● |
| NON-MALIGNANT HEMATOPOIETIC CELLS | | ooo | ooo | ●●● |
| ERYTHROCYTES (A,B,O,Rh+) | | oooo | oooo | |
| | | oooo | oooo | |

*Each circle represents a different cell line. Results:
  o Antigen recognized by this antibody is not present.
  ● Antigen recognized by this antibody is detectable
  ◐ Antigen recognized by this antibody is poorly expressed.
Cell surface antigens assayed by absorption analysis and red cell rossetting technique.
Intracellular components are analyzed by indirect immunofluorescent analysis.

Cell surface antigens assayed by absorption analysis and red cell rossetting technique.
Intracellular components are analyzed by indirect immunofluorescent analysis.

TABLE V
HUMAN MONOCLONAL ANTIBODIES REACTIVE WITH INTRACELLULAR ANTIGENS

| CELL LINES | Ch5-8 | Te39 | Hu44 | Gr431 | Ch13 | Ch45 |
|---|---|---|---|---|---|---|
| BREAST CANCER | ●ooo | oooo | oooo | ●o●o | oo●o | |
| COLON CANCER | o●o● | ●●oo | o●oo | oooo | ●ooo | |
| LUNG CANCER | oooo | oooo | o●oo | oo●o | o●oo | |
| RENAL CANCER | oooo | oooo | ooro | oooo | ooo● | |
| BLADDER CANCER | oooo | ●ooo | oooo | oooo | oo●o | |
| OVARIAN CANCER | ●o● | ooo | ooo | ooo | oo | |
| UTERINE/CERVICAL CANCER | ●o | oo | ●o | ●o | oo | |
| MELANOMA | oooo | oooo | oooo | oooo | oooo | |
| ASTROCYTOMA | oooo | oooo | oooo | oooo | oooo | |
| NEUROBLASTOMA | oo | oo | oo | oo | oo | |
| FIBROBLASTS | ooo | ooo | ooo | ooo | ooo | |

TABLE V-continued

| | HUMAN MONOCLONAL ANTIBODIES REACTIVE WITH INTRACELLULAR ANTIGENS | | | | | |
|---|---|---|---|---|---|---|
| CELL LINES | Ch5-8 | Te39 | Hu44 | Gr431 | Ch13 | Ch45 |
| NORMAL KIDNEY | | o o o o | o o o o | o o o o | o ● ● ● | o o o o |
| MONONUCLEAR CELLS | | o o o | o o o | o o o | o o o | o o o |
| ERYTHROCYTES (A,B,O,Rh+) | | o o o | o o o | o o o | o o o | o o o |

*Each circle represents a different cell line. Results:
  Antigen recognized by this antibody is not present.
  Antigen recognized by this antibody is detectable
  Antigen recognized by this antibody is poorly expressed.
Cell surface antigens assayed by absorption analysis and red cell rossetting technique.
Intracellular components are analyzed by indirect immunofluorescent analysis.

What is claimed:

1. Hybridoma cell lines which produce human monoclonal antibodies which specifically bind to cell surface antigens and intracellular components of human cells, said cell lines selected from the group consisting of HB8565, HB8572, HB8573, HB8574, HB8575, HB8576, and HB8577.

2. Human monoclonal antibodies produced by the cell lines of claim 1.

3. Method of detecting cell surface antigens or intracellular components in human cells comprising contacting said cells with human monomclonal antibodies which specifically bind to said antigens or components wherein said antibodies are antibodies produced by hybridoma cell lines selected from the group consisting of HB8572, HB8573, HB8574, HB8575, HB8576, and HB8577 under conditions favoring formation of antigen-antibody complexes; between said antigens or said components and said antibodies, and determining the presence of said complexes.

4. Method of claim 3 wherein said cells are cultured human cells or excised tissue specimen from an individual, said tissue specimen being fresh, frozen or embedded in wax.

5. Method of claim 3 wherein said cell surface antigen is antigen Ev248 and said antibody is the antibody produced by hybridoma cell line HB8565.

6. Method of claim 3 wherein said intracellular component is contacted by a human monoclonal antibody produced by a hybridoma cell line selected from the group consisting of HB8572, HB8573, HB8574, HB8575, and HB8576.

7. Method of detecting the presence of malignant cells in a sample comprising contacting a cell sample with human monoclonal antibody produced by hybridoma cell line HB8565 which specifically binds to cell surface antigens of malignant cells under conditions favoring formation of antigen-antibody complexes between said antibody and said cell surface antigen and determining the presence of said complexes.

8. Method of claim 7 wherein said cells are in excised tissue, said tissue being fresh, frozen or embedded in wax.

9. Method of detecting epithelial cells in solid tumors comprising contacting an excised sample of a solid tumor with human monoclonal antibody produced by hybridoma cell line HB8565 under conditions favoring formation of complexes between said antibody and antigen on said epithelial cells to which said antibody is specific and determining formation of said complexes.

10. Method of claim 9 wherein said cells are in excised tissue, said tissue being fresh, frozen or embedded in wax.

11. Method of phenotyping a metastasized common or primary tumor for its tissue source comprising contacting a sample of said tumor with human monoclonal antibody produced by hybridoma cell line HB8565 under conditions favoring formation of antigen-antibody complexes between said antibody and antigen on said tumor for which said antiody is specific, and determining the presence of said complexes.

12. A panel for determining the presence of malignant cells comprising at least two monoclonal antibodies from the group consisting of monoclonal antibodies produced by hybridoma cell lines HB8565, HB8572, HB8573, HB8574, HB8575, HB8576, and HB8577.

* * * * *